United States Patent [19]
Burkhart et al.

[11] Patent Number: 6,103,248
[45] Date of Patent: Aug. 15, 2000

[54] TOPICAL PREPARATION AND THERAPY FOR HEAD LICE

[76] Inventors: Craig G. Burkhart; Craig N. Burkhart, both of 4556 Crossfields Rd., Toledo, Ohio 43623

[21] Appl. No.: 09/083,593

[22] Filed: May 22, 1998

[51] Int. Cl.[7] .............................. A61K 7/06; A01N 25/00
[52] U.S. Cl. ......................... 424/401; 424/70.1; 424/405
[58] Field of Search .................................. 424/70.1, 405; 514/947

[56] References Cited

U.S. PATENT DOCUMENTS

| | | | |
|---|---|---|---|
| 4,479,968 | 10/1984 | Hyman et al. | 424/330 |
| 5,026,734 | 6/1991 | Browning | 514/723 |
| 5,288,483 | 2/1994 | Cardin et al. | 424/70 |

OTHER PUBLICATIONS

Consumer Reports, Feb. 1998, pp. 62–63.
Skin & Allergy News, May 1997, p. 32.
Human Lice and Their Management, pp. 298–310, 1995.
Chemotherapy of Parasitic Diseases, pp. 536–537, 1986.
Facts and Comparisons, pp. 584a–586a, 1991.
"Head Lice in Schoolchildren", pp. 471–473, Archives of Diseases in Childhood, Dec. 1996.
Skin & Allergy News, Sep. 1997, p. 14.
"Synergized Pyrethrin Mousse . . . ", Clinical Therapeutics, vol. 16, No. 1, 1994, pp. 57–64.
Human Lice, vol. 4, pp. 1–4, 1989.
"Drugs for Head Lice", The Medical Letter, vol. 39, Jan. 17, 1997, pp. 6–7.
"Save This Important Notice!", National Pediculosis Association, 1996.
"Scanning Electron Microscopy . . . ", Journal of Parasitology, vol. 59, No. 5, Oct. 1973, pp. 913–919.

*Primary Examiner*—Thurman K. Page
*Assistant Examiner*—S. Howard
*Attorney, Agent, or Firm*—MacMillan, Sobanski & Todd, LLC.

[57] ABSTRACT

A topical preparation for applying to scalp hair for the treatment of head lice, the topical preparation including a killing agent effective to kill the head lice, a lipophilic carrier for the killing agent, the carrier including a surfactant effective to allow the topical preparation to be washed out of the hair, and the carrier having a viscosity within a range of from about 10,000 centipoise to about 85,000 centipoise at 21° C. A topical therapy for head lice includes applying the topical preparation to dry scalp hair infested with head lice, and leaving the topical preparation on the hair at least about 15 minutes. The therapy preferably includes applying a second application of the topical preparation about 6–10 days after the first application.

20 Claims, No Drawings

TOPICAL PREPARATION AND THERAPY FOR HEAD LICE

BACKGROUND OF THE INVENTION

This invention relates in general to the treatment of head lice, and in particular to a topical preparation and therapy for head lice.

Head lice is a persistent problem, especially among elementary school-aged children. It was reported that six million U.S. school children will become infested with head lice in one year, that is one out of every four students in elementary schools (*Consumer Reports*, February 1998). The total number of people in the U.S. infested with head lice in one year is about ten million when all ages are accounted for. The incidence of head lice is only slightly improved from the reported incidence in 1940, which was prior to the advent of insecticides and "superior" knowledge by the medical establishment.

Infestation with head lice typically causes itching of the scalp. In some cases, a person may develop lesions or papules on the scalp, swollen glands in the neck or under the arms, or other symptoms. A secondary problem is that many schools have forced absenteeism if a child has any nits (lice eggs) in their hair. Such a "no-nit" policy has negative social implications for the child and parents. Head lice is becoming a sensitive social issue.

Although head lice are not considered vectors for systemic human infection, the evidence strongly supports the possibility that head lice could be vectors. For example, rickettsiae and spirochetes are known to be obtainable from the blood of the host (head lice are blood suckers like mosquitoes); these organisms multiply in the gut of the head lice, and are also found in high numbers in their feces. Viruses, like the AIDS virus, also can be found in the gut and feces of head lice, but these organisms do not multiply in the gut of the louse; thus, the number of viruses in the feces would not be high. However, any organism in the blood of the host would be found in the feces of the louse, and thereby, could be potentially transmitted when the louse finds a new host, i.e., a new human being to infest.

Current commercial treatments for head lice include applying an insecticide on the scalp hair to kill the head lice. The pharmaceutically formulated insecticides are universally admixed in a water-based composition such as a shampoo, cream or lotion. Home remedies for head lice include applying petroleum jelly or mayonnaise on the scalp hair to smother the head lice. Unfortunately, these treatment methods have not been totally effective. Thus, it would be desirable to provide a topical preparation and a topical therapy in the treatment of head lice which are more effective than the current methods for treating head lice. With government restrictions on the available insecticides for treatment of head lice, unless a better delivery system is developed, the likelihood of resistance to insecticides will increase and more toxic insecticides may have to be used. This is especially true given the increased resistance that various cities are presently reporting. There is clearly a need for a safe, effective substitute for the present treatment regimens.

SUMMARY OF THE INVENTION

The present invention relates to a topical preparation for applying to scalp hair for the treatment of head lice. The topical preparation includes a killing agent such as an insecticide effective to kill the head lice, and a lipophilic carrier for the killing agent. The carrier includes a surfactant effective to allow the topical preparation to be washed out of the hair. The carrier has a viscosity within a range of from about 10,000 centipoise to about 85,000 centipoise at 21° C. Preferably, the carrier by itself is effective to kill the adult head lice and the killing agent is effective to kill the lice eggs. The present invention also relates to a topical therapy which includes applying the topical preparation to dry scalp hair infested with head lice. Preferably, the topical preparation is applied so that the hair is totally saturated with the topical preparation. The topical preparation is left on the hair at least about 15 minutes. Preferably, the topical preparation is left on the hair overnight and the treated person changes clothes afterwards. A second application of the topical preparation is preferably applied about 6–10 days after the first application.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Although head lice has been a problem for many years, previous methods for treating head lice have not been totally effective. This invention is based on several discoveries we have made while researching the anatomy and physiology of head lice, and the deficiencies associated with the previous methods for treating head lice.

As discussed above, current prior art commercial preparations for head lice include an insecticide admixed in a water-based composition. During our research on head lice, we have discovered that the spiracles by which adult head lice breathe, and the opercula by which lice larvae in the egg exchange oxygen, automatically close when exposed to water. This is not the case when the spiracles and opercula are exposed to a lipophilic composition such as an oil-based composition. We believe that when these breathing apparatuses are closed, the insecticide in the composition is less able to penetrate the exterior of the lice and eggs. As a result, the water-based commercial compositions are not completely effective in killing the lice and eggs. On the other hand, we believe that when the breathing apparatuses are open, the insecticide in the composition very effectively penetrates the exterior of the lice and eggs to provide a killing action to the neural and muscle tissue which is the site of insecticidal activity. To maximize killing of the lice and eggs, our invention includes a killing agent such as an insecticide admixed in a lipophilic carrier. Thus, we have invented a new topical delivery system to eradicate head lice, both the adult head lice and the lice eggs.

We have noted that commercial insecticide compositions do not kill all the lice eggs. Previously, we believed that the main reason for the inability of insecticides to eradicate all the eggs is that the central nervous system of the louse larva, which is the pharmaceutical location of insecticide action, is underdeveloped until the fifth day of existence. Our new research indicates that the larva in the egg is surrounded by several lipid membranes. We have confirmed these lipid layers by two methods: histochemical analysis and freeze-fracture technique with scanning electron microscopy. From our findings, it appears that a successful ovicidal product must penetrate the lipid layers as well as the operculum. The lipophilic carrier of our invention greatly facilitates the penetration of the insecticide through the lipid layers to kill the larva. The lipid composition from which arises the neuronal membranes is plentiful in the egg even in the early stages of egg development. Thus, if the insecticide gets through the operculum, through the lipid membranes, and to the lipids in the developing larval egg, we should produce 100% ovicidal kill.

The topical preparation of our invention includes a thick, lipophilic carrier to effectively kill both the adult lice and the lice eggs. The lipophilic carrier has a hydrophilic/lipophilic balance ("HLB") of less than 10, preferably not greater than about 8.5, and more preferably not greater than about 6. As discussed above, the lipophilic carrier enables the topical preparation to effectively penetrate and kill the lice eggs.

The carrier is thick so that the topical preparation stays on the hair and does not run off, and thereby stays in contact with the adult lice and lice eggs long enough to kill them. Also, the thick carrier insures that the topical preparation cannot be removed from the louse when the infested person washes out the topical preparation from his hair. Furthermore, the entire length of each hair follicle is saturated with the topical preparation by our method. This could be important because even though most lice eggs are laid one millimeter from the scalp, some female lice have been known to lay their eggs much further out from the scalp surface. Thus, all potential eggs in the person's hair are treated. Head lice can smell insecticides and will try to avoid direct contact with the insecticide (i.e. a flee response). A thick carrier insures saturation of the hair and prevents the head lice from avoiding contact with the insecticide due to insufficient application of the insecticidal agent. Advantageously, the thick lipophilic carrier is believed to be more effective than water or alcohol carriers in masking the scent of the pesticide. Another advantage is that the thick carrier is more effective than a liquid carrier in killing the adult head lice by smothering them. Preferably, the carrier by itself is effective to kill the adult head lice. The killing agent of the topical preparation kills the lice eggs for total eradication of the problem. (We have found that the lice eggs are not killed by smothering, which explains why home remedies such as petroleum jelly or mayonnaise are not totally effective in killing the head lice.) The thickness of the carrier is measured by a viscosity within a range of from about 10,000 centipoise to about 85,000 centipoise at 21° C., preferably within a range of from about 25,000 centipoise to about 75,000 centipoise, and more preferably within a range of from about 25,000 centipoise to about 65,000 centipoise. The carrier is too thick and hard to apply to the hair at higher viscosities.

Head lice live on the surface of the scalp and on the scalp hair. The topical preparation should provide a reservoir effect, keeping the insecticide on the surface of the scalp and on the hair structures. The thickness of the carrier enhances this reservoir effect.

The carrier can be any medium having the required lipophilicity and thickness, such as ointments, emulsions and suspensions. For example, suitable lipophilic carriers can include ointments such as oleaginous ointments, water-in-oil emulsion ointments, absorption ointments and inert ointments. Water soluble ointments (e.g., polyethylene ointment and carbowax) are not suitable because they are not lipophilic. Other suitable carriers can include emollients, creams, gels and pastes. These can also be called numerous other names such as night creams, lubricant creams, moisturizing creams, cold creams, emollient creams, and transparent creams. Other suitable carriers can include complex emulsion systems in which there is a multiple phase dispersion. The lipophilic carrier usually contains one or more oils, and in some embodiments it contains greater than about 50% oil. One preferred mixture of oils is petrolatum (also called mineral jelly) mixed with liquid petrolatum (also called mineral oil). Mineral oil is unsuitable alone because it is not thick enough. However, mineral oil mixed with a thickener such as wax can be used as the carrier if suitably thickened. Mineral oil can be gelled, for example, with the addition of a polyethylene, producing a soft material resembling white petrolatum. The carrier can be thickened by the addition of any suitable thickener such as waxes, gums, clays, corn starch, or sorbitol. Other suitable oils for use in the carrier, if suitably thickened, include triglycerides such as caprylic/capric triglyceride, and isopropyl myristate.

The carrier also includes a surfactant effective to allow the topical preparation to be washed out of the hair. The thickness of the carrier makes it very difficult to wash out of the hair without the addition of the surfactant. Preferably, the topical preparation can be substantially washed out of the hair with two washings. The surfactant preferably has a hydrophilic/lipophilic balance ("HLB") within a range of from about 4 to about 12. Some specific examples of suitable surfactants include polysorbate 60, oleth-5, oleth-10, and ceteareth-20. The surfactant preferably comprises a mixture of a hydrophilic surfactant and a lipophilic surfactant. (When a mixture of surfactants is used, the weighted average HLB is within the 4–12 range.) For example, the surfactant mixture can include a polysorbate such as Tween 80 (HLB 15) and a sorbitan ester such as Span 80 (HLB 4), the surfactants being mixed to provide a weighted average HLB of about 10. Other polysorbates such as Tween 20 or Tween 40 could be used in place of the Tween 80. Another example of a suitable surfactant mixture is a polyethylene monostearate (HLB 15) and a glycerol monostearate (HLB 4). Preferably, the surfactant used is a nonionic surfactant to avoid any interference of the surfactant with the insecticide. The surfactant is preferably incorporated in an amount within a range of from about 10% to about 20% surfactant by weight of the carrier.

The carrier can also include a wide variety of optional ingredients. A preferred optional ingredient is an attractant for the head lice, such as ammonia. An attractant may be helpful because lice tend to flee the scalp before the scalp hair can be totally saturated with the topical preparation, especially the small nymph stages of the lice. The attractant would thus reduce the chance of later reinfestation or fomite transmission of any louse that might try to flee during application of the topical preparation. The lipophilic carrier by itself is believed to attract the head lice because the lice are dependent on the presence of oils (such as scalp oils) to avoid dehydration. Other optional ingredients include an antioxidant such as tocopherol, a preservative such as methylparaben or propylparaben, glycerine, and sorbitol.

The killing agent admixed in the carrier includes any material effective in killing the head lice. Preferably, the killing agent is an insecticide. The following insecticides, as well as others not listed, are suitable for use in the topical preparation: gamma benzene hexachloride, malathion, permethrin, pyrethrin, piperonyl butoxide, ivermectin, moxidectin, other macrocyclic lactones such as compound F28249, doramectin, pyrantel pamoate, fenbendaxole, oxibendazole, benzimidazole, thiabendazole, abamectin, avermectin, carboxyl, DDT (chlorophenothene), cromiton, benzyl benzoate, temephos, coumaphos, diazinon, sumithrine, fluorescein, pyrantel embonate, carbophenothion, chlorfenvinphos, crotoxyphos, fenitrothion, derris, bromocyclen, diflubenzuron, organophosphates, organochlorines, hexachlorocyclohexanes, crotoxyphos (plus dichlorvos), stirofos, tetrachlorvinphos, dioxathion, phosmet, bromocyclen, famphur, fenthion, methoxychlor, toxophene, trichlorfon, cypermethrin, bioallethrin, cyano substituted pyrethroid, phenothrin, pirimiphos methyl, carbaryl, propoxur, temephos, nicotine, pralidoxine, parathion, and natural oils such as coconut oil, anise, ylang ylang, garlic and lavender. Preferably, the insecticide is lipophilic so that it can more readily pass through the lipophilic membranes surrounding the louse larva in the egg. Some examples of preferred killing agents are botanical agents (e.g., pyrethrin, anise, ylang ylang), synthetic derivatives of botanical agents (e.g., permethrin), and chemical insecticides (e.g., organochorines, organophosporates, carbamates, anticholinesterases). It is preferred to use insecticides that are allowed on formulary by the FDA. The amount of insecticide in the topical preparation is usually within a range of from about 0.5% to about 10% insecticide by weight of the topical preparation. The insecticide can usually be simply mixed into the topical preparation.

Preferably, the concentration of killing agent in the topical preparation, and the frequency of application of the killing agent, are not greater than conventionally utilized in lice therapeutics. Advantageously, the lipophilic carrier of this invention allows the option of using a reduced concentration of killing agent to effectively kill the head lice. In other words, the concentration of killing agent in the topical preparation can be less than the concentration previously required for therapeutic action. Consequently, insecticides can be used that were not previously allowed, or that were previously discontinued as requiring too high a topical dosage. The reduced concentration reduces the concern about toxicity of the insecticide, and reduces the problem of the head lice becoming tolerant to the insecticide. Resistance to insecticides by the adult louse will not be a factor with this treatment as no louse will be able to escape the thick lipophilic base in our formulation. Thus, the product used appropriately will assure 100% kill of adult lice. Of course, the topical preparation is not limited to concentrations of killing agent which are not greater than previously used concentrations. For example, if a higher concentration of an insecticide is approved for over-the-counter or prescription use, it may be desirable to use the higher concentration to maximize the effectiveness of the topical preparation.

One of the reasons for the failure of water-based, or alcohol-based, insecticides is the fact that they are highly diluted by patients. An average shampoo of a person with moderately short hair length uses between 100 ml and 150 ml of water to wet the hair, and 5 ml of the insecticidal shampoo to work up a good lather. Thus, the insecticide becomes a 1:20 to 1:30 dilution. Furthermore, a person with longer hair may use considerably more water, increasing the dilution even more. Our product is applied without water and, therefore, is undiluted.

This invention also includes a topical therapy which treats the head lice infestation with respect for the disease it truly is. The patient is not only treated with the effective topical preparation of the invention, but the patient is also given instructions so that he appreciates that total adherence to a therapy plan is necessary to eradicate the condition. Our treatment program will avoid the overtreatment problem that is presently occurring with some over-the-counter and prescription therapies because (1) the treatment will be much more effective, (2) the treatment program will be spelled out, and (3) the treatment program is likely to be completed correctly the first time.

The topical therapy involves applying the topical preparation to dry scalp hair infested with head lice. The patient is instructed to leave the topical preparation on the scalp hair at least about 15 minutes to allow time for the insecticide to kill the adult lice and lice eggs. Preferably, the topical preparation is left on the scalp hair at least about one hour, and more preferably at least about 3–4 hours. Current commercial compositions do not leave the insecticide on long enough to effectively kill the adult lice and lice eggs. In a particularly preferred therapy, the topical preparation is left on the scalp hair overnight. The topical preparation can be held on the scalp hair by use of a shower cap or other suitable containment device. By suggesting leaving the topical preparation on the scalp hair overnight, we make sure that the patient allows the topical preparation to stay in the hair for an adequate time period, but we also insure that the patient will be putting on new clothes after the treatment (because the old clothes may have a few lice nymphs on them, potentially leading to reinfestation).

Enough topical preparation is applied to totally saturate the scalp hair with the topical preparation. Preferably, at least about 50 ml of topical preparation is applied to totally saturate the hair. The saturated hair is totally greased down into an oily, matted mass. This will reduce the problem with current commercial compositions in which people are not sufficiently saturating their hair with insecticide. By totally saturating the hair, all the hair from the roots to the tips will be inundated with the insecticide, and thereby, eliminating the possibility of resistance developing as this prolonged application assures death of all adult lice.

Preferably, a second application of the topical preparation is done about 6–10 days after the first application. The second application will increase the ovicidal kill in case the first application was not 100% ovicidal. More importantly, the second application will reduce the potential of reinfestation. We believe that there are many lice present in the homes and furniture of families with head lice infestations. Most people infested with head lice have about 20 adult lice in their hair. Inasmuch as a female head louse lays about 200 eggs per month, and given that the small nymphs are barely visible to the naked eye, we believe that there are a lot of young lice always looking for a new host. These nymphs are forced to flee the "nest" and hope to find a new home before they dehydrate. The second application of the topical preparation will prevent reinfestation by these nymphs. More preferably, a third application is done about 6–10 days after the second application.

The topical therapy for the treatment of head lice preferably includes four aspects:
1. killing the adult head lice,
2. killing the lice eggs,
3. treating all members of the affected family and close contacts with the topical preparation unless examined thoroughly and proven to be lice-free, and
4. treating the environment so that fomite spread does not occur. This includes such procedures as machine washing in hot water and drying (or dry cleaning) clothing, headgear, scarves, coats, bed linens, etc. Personal articles that may not be easily washed can be sealed in a plastic bag for two weeks. Thorough vacuuming of rooms inhabited by infected patients can also be done.

EXAMPLE 1

A topical preparation according to the invention was prepared by mixing permethrin (1% by weight of the topical preparation) and a lipophilic carrier (99% by weight). The carrier was a commercial gel hair conditioner called "Proclaim Professional Care Conditioning Hair", manufactured by Brentwood Beauty Labs International, Hillside, Ill. The carrier contained the following ingredients (listed in order from largest ingredient to smallest ingredient): petrolatum, mineral oil, paraffin wax, bergamot oil, colors and fragrance (the carrier was very lipophilic, being comprised substantially of oils). The carrier had a viscosity of approximately 60,000 centipoise at 21° C. A surfactant such as a Tween 80/Span 80 mixture (HLB about 10) would be added to the carrier, in an amount of about 15% surfactant by weight of the carrier, to allow the topical preparation to be more easily washed out of the hair.

The topical preparation was used to treat patients infested with head lice. The patients applied the topical preparation to dry scalp hair in sufficient amount to totally saturate the hair with the topical preparation. The topical preparation was left on the scalp hair overnight, and was held in place by the use of a shower cap. In the morning, the patients washed the topical preparation from the hair and changed into new clothes. The patients repeated the application seven days after the first application. After two treatments, no adult lice were noted and neither were any instars (young lice). There were still egg castings present but no viable young from these nits were appearing. The patients, therefore, had achieved clinical cure. In clinical trials with this topical preparation of approximately 20 elementary school children brought to my office because of treatment failure with at least two of the over-the-counter products, our product has been totally successful in each case to date In all these previously resistant cases, the topical preparation appears to kill the adult lice as well as the eggs. Our follow-up has been with the families as well as with the school nurses.

EXAMPLE 2

A topical preparation according to the invention was prepared by mixing permethrin (1% by weight of the topical preparation) and a lipophilic carrier (99% by weight). The carrier was a commercial gel pomade called "Sportin' Waves", manufactured by Soft Sheen Products, Inc., Chicago, Ill. The carrier contained the following ingredients (listed in order from largest ingredient to smallest ingredient): petrolatum, deionized water, ceteareth-20, glycerine, mineral oil, polysorbate 60, oleth-5, propylene glycol, paraffin, hydroxylated lanolin, oleth-10, microcrystalline wax, fragrance, methylparaben, propylparaben, and simethicone. The carrier had a viscosity of approximately 80,000 centipoise at 21° C., and a hydrophilic/lipophilic balance of approximately 10–11. The topical preparation should be effective for treating head lice according to the invention.

EXAMPLE 3

The topical preparation and treatment method described in Example 1 are used to treat head lice, except the topical preparation is left on the scalp hair one hour instead of overnight. The topical preparation and treatment should be effective for treating head lice according to the invention.

EXAMPLE 4

The topical preparation and treatment method described in Example 1 are used to treat head lice, except the patients are treated once with the topical preparation instead of twice. The topical preparation and treatment should be effective for treating head lice according to the invention.

EXAMPLE 5

The topical preparation and treatment method described in Example 1 are used to treat head lice, except the topical preparation is formulated to have a viscosity of approximately 25,000 centipoise at 21° C. by the use of a higher amount of mineral oil and lower amounts of petrolatum and paraffin wax. The topical preparation and treatment should be effective for treating head lice according to the invention.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A topical preparation for applying to scalp hair for the treatment of head lice, the topical preparation comprising:
   a killing agent effective to kill the head lice,
   a lipophilic carrier for the killing agent, the carrier containing a surfactant effective to allow the topical preparation to be washed out of the scalp hair, and the carrier having a viscosity within a range of from about 10,000 centipoise to about 85,000 centipoise at 21° C.

2. The topical preparation defined in claim 1 wherein the killing agent is an insecticide.

3. The topical preparation defined in claim 1 wherein the carrier by itself is effective to kill adult head lice.

4. The topical preparation defined in claim 1 wherein the surfactant has a hydrophilic/lipophilic balance within a range of from about 4 to about 12.

5. The topical preparation defined in claim 1 wherein the surfactant comprises a mixture of a hydrophilic surfactant and a lipophilic surfactant.

6. The topical preparation defined in claim 1 wherein the surfactant is a nonionic surfactant.

7. The topical preparation defined in claim 1 wherein the carrier has a viscosity within a range of from about 25,000 centipoise to about 65,000 centipoise at 21° C.

8. The topical preparation defined in claim 1 wherein the surfactant is present in an amount within a range of from about 10% to about 20% surfactant by weight of the carrier.

9. The topical preparation defined in claim 1 wherein the carrier has a hydrophilic/lipophilic balance of not greater than about 8.5.

10. A topical therapy for head lice comprising applying a first application of a topical preparation to dry scalp hair infested with head lice, and leaving the topical preparation on the scalp hair at least about 15 minutes, the topical preparation comprising a killing agent effective to kill the head lice, a lipophilic carrier for the killing agent, the carrier containing a surfactant effective to allow the topical preparation to be washed out of the scalp hair, and the carrier having a viscosity within a range of from about 10,000 centipoise to about 85,000 centipoise at 21° C.

11. The topical therapy defined in claim 10 additionally comprising applying a second application of the topical preparation about 6–10 days after the first application.

12. The topical therapy defined in claim 11 additionally comprising applying a third application of the topical preparation about 6–10 days after the second application.

13. The topical therapy defined in claim 10 wherein the topical preparation is applied so that the scalp hair is totally saturated with the topical preparation.

14. The topical therapy defined in claim 10 wherein the topical preparation is left on the scalp hair at least about one hour.

15. The topical therapy defined in claim 10 wherein the topical preparation is left on the scalp hair overnight.

16. The topical therapy defined in claim 10 wherein the treated person changes clothes after application of the topical preparation.

17. The topical therapy defined in claim 10 wherein the topical preparation is applied so that the scalp hair is totally saturated with the topical preparation, the carrier by itself is effective to kill adult head lice, and the killing agent is effective to kill lice eggs to prevent reinfestation.

18. The topical therapy defined in claim 10 wherein the surfactant has a hydrophilic/lipophilic balance within a range of from about 4 to about 12.

19. A topical preparation for applying to scalp hair for the treatment of head lice, the topical preparation comprising:

a killing agent effective to kill the head lice, a lipophilic carrier for the killing agent, the carrier containing a surfactant effective to allow the topical preparation to be washed out of the scalp hair, and the carrier having a viscosity within a range of from about 25,000 centipoise to about 85,000 centipoise at 21° C.

20. The topical preparation defined in claim 19 wherein the carrier has a hydrophilic/lipophilic balance of not greater than about 8.5.

* * * * *